United States Patent

Zewert et al.

Patent Number: 5,338,428
Date of Patent: Aug. 16, 1994

[54] POLY(N-ACYLALKYLENIMINE) ELECTROPHORESIS SUPPORT MEDIA

[75] Inventors: Thomas Zewert, Pasadena; Michael G. Harrington, La Canada, both of Calif.

[73] Assignee: California Institute of Technology, Pasadena, Calif.

[21] Appl. No.: 69,075

[22] Filed: May 28, 1993

[51] Int. Cl.$^5$ ............................................. C25B 9/00
[52] U.S. Cl. .......................... 204/299 R; 204/187.8; 525/410; 525/411; 525/540; 524/813; 524/916
[58] Field of Search ..................... 525/410, 411, 540; 524/813, 916; 204/182.8, 299 R

[56] References Cited

U.S. PATENT DOCUMENTS 4,006,069  2/1977  Hiratsuka et al. ............... 204/180 G
5,055,517  10/1991  Shorr et al. .......................... 524/813

OTHER PUBLICATIONS

Borek Janek, Gelman Sciences, Inc., "Electrophoresis", Encyclopedia of Polymer Science and Engineering, vol. 5, 1985, pp. 772–792.

Primary Examiner—John Niebling
Assistant Examiner—C. Delacroix-Muirheid
Attorney, Agent, or Firm—Poms, Smith, Lande & Rose

[57] ABSTRACT

Electrophoresis support media which include one or more poly(N-Acylalkylenimine) polymers (PAEI). The polymers have the formula

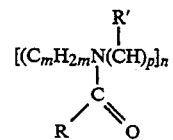

wherein m and p are between 1 and 3, n is between about 100 and 10,000, where R is an alkyl, perfluoroalkyl or phenyl group and wherein R' is H or an alkyl group. These polymers can be used in place of polyacrylamide gels, agar gels and agarose gels. PAEI polymers may be cross-linked with various cross-linking agents to provide electrophoresis support media with a wide range of pore sizes and physical strength.

19 Claims, 3 Drawing Sheets

POLY(N-ACYLALKYLENIMINE) ELECTROPHORESIS SUPPORT MEDIA

BACKGROUND OF THE INVENTION

The present invention was made with the support of the National Science Foundation Grant No. DIR-8809710. The United States Government may have rights to the invention.

1. Field of the Invention

The present invention relates generally to the support media used in electrophoresis. More particularly, the present invention is directed to the use of a poly(N-acylalkylenimine) s as at least part of the support media.

2. Description of Related Art

Support media are commonly used in electrophoresis systems to suppress convection caused by gravity, thermal gradients or concentration gradients. The support media which have been used conventionally include powdered and porous solids, fibrous materials and gels. The powdered and porous materials which are used as electrophoresis media includes cellulose, starch, silica, glass, polyurethane foam and glass powder. For the most part, the powdered and porous solid electrophoresis media have been replaced by gels which have a higher resolving power. The powdered and porous solids are generally reserved for large scale preparative separations.

Fibrous materials, such as paper have been used in electrophoresis for many years. Paper electrophoresis support media became popular due to their low cost and ease of handling. However, the use of paper as a support media has largely been replaced with gels due to problems experienced with variations in different batches of paper and impurities in the paper which caused undesirable and unpredictable absorptive properties.

Cellulose acetate membranes have also been used as an electrophoresis support media. Cellulose acetate membranes do not have the undesirable absorptive properties of paper and have a uniform microporous structure and are chemically inert. However, cellulose acetate must be laminated to a flexible plastic support due to the inherent brittleness of dry cellulose acetate.

The most popular electrophoresis support materials are based on molecular-sieve gels. Starch gels were initially used in the early 1950's for the separation of proteins. However, the narrow range of porosities and the fragile nature of starch gels have rendered them obsolete. Agar and agarose gels have been widely used as an electrophoresis support media. Agar and agarose gels are obtained from polysaccharides extracted from red algae. Agar and agarose gels have not been widely used (except for large DNA molecules) as an electrophoresis support media because of limited sieving properties and a high content of anionic residues, such as sulfate and pyruvate.

Polyacrylamide gel (PAG) has been widely adopted as the support media of choice for the separation of both proteins and DNA. Cross-linked polyacrylamide provides good resolution in many applications because it possesses sieving as well as anti-convective properties. The sieving properties of cross-linked polyacrylamide gels are particularly well-suited for molecular weight separations. By varying the percentage of monomer or cross-linker, the nature of the gel can be changed to suit a variety of separations from small (1,000 kD) peptides to large (500,000 kD) proteins.

Despite the numerous advantages and popularity of polyacrylamide gel support media, there are a number of inconveniences, hazards and limitations which accompany the use of this material. For example, the acrylamide monomer and the bis-acrylamide cross-linker represent a serious health hazard. Although the polymer is not toxic, exposure to the monomer and cross-linker during preparation of the gel poses significant health concerns. In addition, residual and derivative chemicals present during post-electrophoresis processing also pose health concerns.

The health problems associated with acrylamide monomer are compounded by the fact that the toxic effects of acrylamide are cumulative. The toxicity problem associated with acrylamide monomers can be carefully controlled in a research setting. However, toxicity concerns may limit the use of polyacrylamide gel in clinical laboratory settings where people being exposed to the toxins may not be well-informed about the risks associated with polyacrylamide monomer and carefully trained with respect to proper handling procedures.

Another problem associated with polyacrylamide gel support media is the difficulty in forming gels of reproducible properties. Acrylamide monomers and the bis-acrylamide cross-linkers are commercially available as extremely pure and uniform compositions. However, separation of the electrophoresis support media involves a high degree of skill and care. Slight changes in preparation technique from batch to batch results in the formation of gels having slightly different properties. Further, the pouring process for preparation of the gel is prone to minor variations which result in the formation of gels which vary in composition at different locations within the gel.

The variability present in polyacrylamide gel support media results in inconsistent protein migration within a particular gel media. Further, protein migration is not reproducible when different batches of gel are used. As a result of these inconsistencies, polyacrylamide gel support media has not been widely used in clinical applications. Instead, cellulose acetate membranes have been used even though they have considerably less resolution power.

Two dimensional electrophoresis (2DE) is a technique which allows the identification of thousands of molecules simultaneously. In 2DE systems, the samples are subjected to electrophoresis based on two independent variables such as charge and mass. For example, in a first dimension, isoelectric focusing (IEF) is used to separate complex mixtures based on charge. In a second dimension, polyacrylamide gel electrophoresis is used to separate the samples based on mass. The resulting 2-dimensional image contains the positional coordinates and quantity of each species as well as all interconnecting correlations. Unlike a series of one-dimensional separations, the 2DE gel image provides a data base which is suitable for determining individual differences between samples and for the analysis of molecular networks.

The full potential of two-dimensional electrophoresis has been difficult to obtain because of non-uniformities in the polyacrylamide gel support media. For example, the computer matching of up to thousands of protein spots on a two-dimensional electrophoresis is greatly hindered by artifacts in the polyacrylamide gel support media such as bubbles, insoluble material, polymer concentration gradients and cross-link density variabilities. These variabilities or artifacts in the gel give rise to glitches in protein spot structure and gel-to-gel variations in composition that result in irreproducibility of relative protein or DNA migration velocities.

In view of the above drawbacks in existing electrophoresis support media, there is a continuing need to provide new support media which overcome the disadvantages set forth above.

SUMMARY OF THE INVENTION

In accordance with the present invention, electrophoresis support media are provided which overcome many of the above-mentioned problems associated with existing support media. The electrophoresis support media of the present invention are non-toxic and well-suited for use in a variety of electrophoresis separations, such as isoelectric focusing and DNA separations. The media are relatively simple to prepare utilizing conventional polymerization procedures and result in the formation of support media having uniform characteristics which are reproducible.

The present invention is based upon the discovery that hydrogels and amphigels composed of poly(N-acylalkylenimine)s (PAEI) may be used as an electrophoresis support media.

The poly(N-acylalkylenimine)s which are useful as electrophoresis media include polymers having the formula

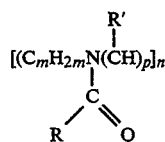

where m and p are between 1 and 3, n is between about 100 and 10,000, where R is an alkyl, perfluoroalkyl or phenyl group and wherein R' is H or an alkyl group.

The PAEI polymer gels in accordance with the present invention may be polymerized and cross-linked to different degrees with different cross-linking agents to provide electrophoresis support media ranging from viscous liquids to gels. As a result, a wide range of electrophoresis media can be prepared which have a variety of separation characteristics. As a feature of the present invention, very little chain transfer or termination occurs during polymerization of N-acylalkylenimines. Accordingly, the formation of PAEI polymer gels can be controlled more closely than the polymerization of existing electrophoresis polymer media.

The ability to closely control polymerization allows the formation of uniform block copolymers composed of different N-acylalkylenimine monomer groups. These highly uniform block copolymers provide different domains of physical properties on a molecular scale which are capable of providing uniform and reproducible separation characteristics. In addition, other structures formed including telechelics (Park, I., Han, I., and Saegusa, T., (1991) *Die Angewandte Makromulekulqre Chemie* 190, 165) and star poly (Dvorak, A. and Schulz, R., (1991) *Makromol. Chem.* 192, 437). These structures can also be use to provide control of the microstructure of the PAEI matrix. For example, the molecular weight of each polymer chain can be highly controlled. When telechelics are cross-linked by the ends, the distance between cross-links is highly controlled.

The electrophoresis support media polymers in accordance with the present invention avoid the problems associated with gels made from naturally occurring materials, such as agarose and agar, and also avoids many of the problems associated with polyacrylamide gels. Accordingly, the electrophoresis support media of the present invention will not only be useful for high performance electrophoresis, but will also be useful in a wide variety of settings where a stable, uniform and reproducible electrophoresis is required.

The above-discussed and many other features and attendant advantages of the present invention will become better understood by reference to the following detailed description.

DETAILED DESCRIPTION OF THE PREFERRED EMBODIMENTS

Figure 1:
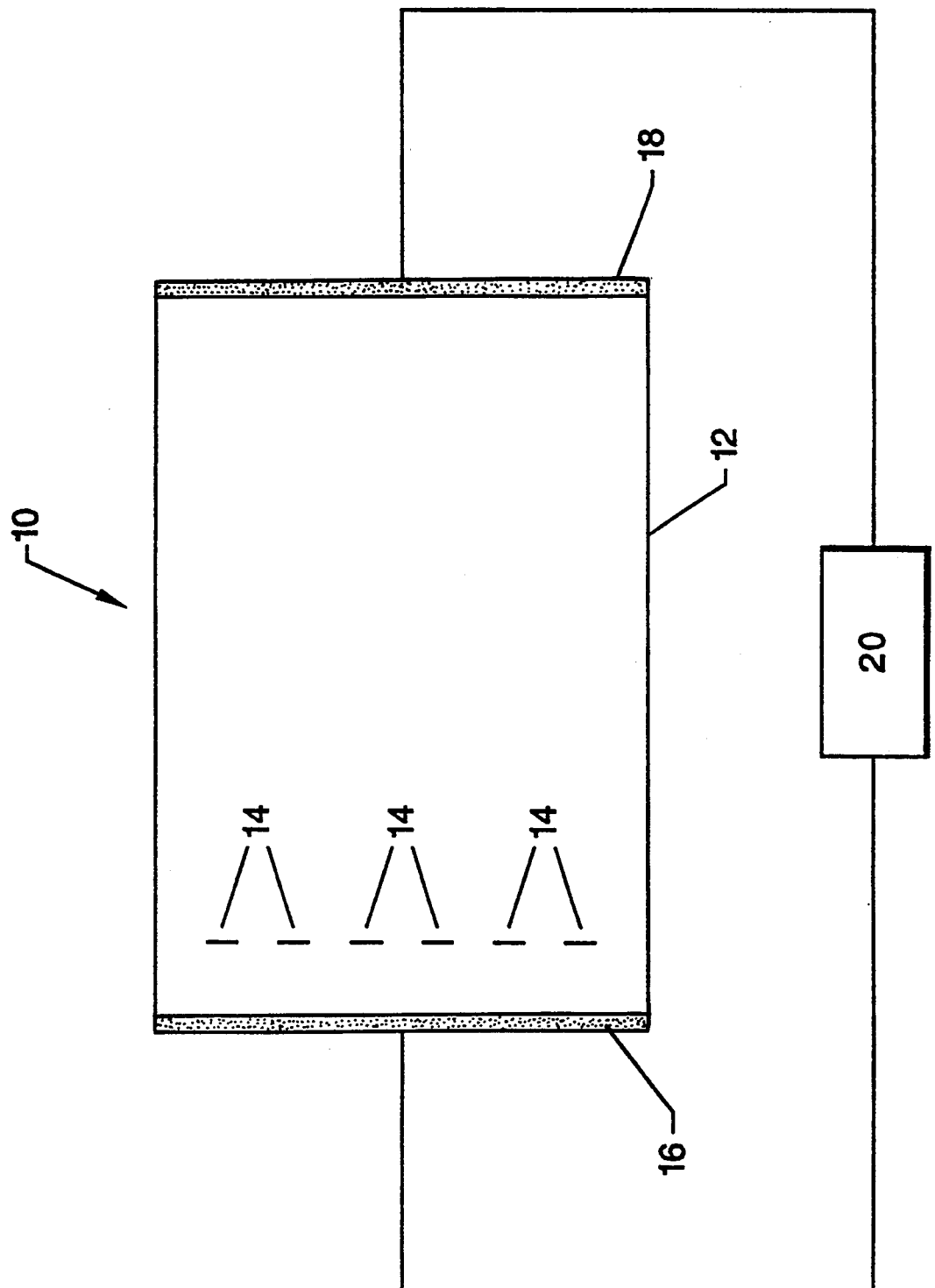
FIG. 1 is a simplified representation of an exemplary electrophoresis gel in accordance with the present invention.

The present invention involves the use of poly(N-acylalkylenimine)s (PAEI) as electrophoresis support media. The various support media encompassed by the present invention may be used in a wide variety of electrophoresis systems as a substitute for cellulose acetate, agarose gel, agar gel, polyacrylamide gel or other conventional support media. The support media encompassed by the present invention can be formed into slabs, columns, or any of the other well-known shapes typically employed in gel electrophoresis systems ranging from capillary zone electrophoresis to industrial scale electrophoresis.

The electrophoresis support media of the present invention is composed of one or more PAEI polymers which have the formula

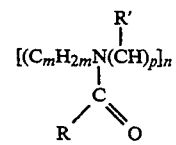

where m and p are between 1 and 3, n is between about 100 and 10,000, where R is an alkyl, perfluoroalkyl or phenyl group and wherein R' is H or an alkyl group. Preferably, m and p will be 1, 2 or 3 and n will be between about 100 and about 10,000. Exemplary PAEI polymers include those where R is methyl, ethyl, propyl, —CF$_3$, —C$_2$F$_5$, —C$_3$F$_7$ and —C$_7$F$_{15}$. R can also be a phenyl group such as —C$_6$H$_5$, —p—NO$_2$C$_6$H$_4$ or —p—CH$_3$C$_6$H$_4$. The alkyl groups used for R and R' may have from 1 to 20 carbon atoms. A preferred polymer is poly(N-acylethylenimine) where m and p are 1, R is methyl and R' is hydrogen.

The electrophoresis polymer gels of the present invention may be prepared according to conventional synthesis procedures. The two preferred synthetic routes involve the ring-opening polymerization of 2-substituted-2-oxazolines or the acylation of a polyalkylenimine- The ring-opening synthesis is described in Kagiya, T., Narisawa, S., Maeda, T., and Fukui, K. (1966) *J. Polymer Science B* 4, 441. Commercial sources of polyalkylenimines are available; however, the commercially available polymers tend to be highly branched at the backbone nitrogen. This is not suitable for some electrophoresis applications because the tertiary nitrogens become charged and may lead to endosmotic effects. It is preferred that the polymers be linear polymers. The ring-opening synthesis is preferred because the molecular weight distributions of the polymer chains can be controlled. When air and water are excluded during the polymerization, very little chain transfer or termination occurs. Thus, the polymerization is "living" and can be controlled more closely than the other polymers which are presently being used for electrophoresis (Szwarc, M. (1956) Nature, 1168; and Higashimura, T. and Sawamoto, M. (1984) Adv. Polym. Sci. 62, 49).

The degree of polymerization may be varied widely depending upon the type of sample being separated by electrophoresis and the desired result. Polymerization of the monomers can be terminated in accordance with well known procedures to provide support media ranging from viscous solutions to gels. Molecular weight ranges for the polymers will normally vary from 10,000 to 500,000. The monomers may be polymerized by solution polymerization, bulk polymerization or any of the other conventional polymerization processes. The support media of the present invention may be used to form electrophoresis gel slabs which vary in size from $1 \times 1$ centimeter up to $40 \times 40$ centimeters. The thickness of the gel slab can vary from relatively thin gels having a thickness of 0.1 mm up to relatively thick gels having thicknesses on the order of 1.0 cm. The gels may be formed into columns ranging in length from 1 cm to 100 cm and having diameters on the order of 0.01 mm to 10 cm.

A simplified representation of an electrophoresis system in accordance with the present invention is shown generally at 10 in FIG. 1. The system includes an electrophoresis support media 12 which includes a PAEI polymer gel. Sample receiving locations or wells 14 are located towards one end of the support media 12. Electrodes 16 and 18 are located on opposite sides of the gel slab. The electrodes are connected to an electrophoresis power pack 20 as is conventionally known. The simplified electrophoresis system 10 is exemplary only. It will be understood by those skilled in the art that the PAEI polymer gels in accordance with the present invention are suitable for use in a wide variety of electrophoresis based separation procedures including two dimensional electrophoresis and isoelectric focusing.

The viscosity of the electrophoresis media in accordance with the present invention may be controlled to provide media ranging from viscous solutions to medium or high density gels. The viscosity of the solutions is controlled by the cross-link density and original molecular weight of the polymer. When media in the form of viscous solutions are desired, the crosslink density is preferably between about 0 and 1%. For medium to high density gels, the cross-link density may range from 0 to 25%

Any of the above mentioned polymers may be used alone or in combination to form a homopolymer or copolymer which may be used as an electrophoresis support material. In addition, cross-linking agents may be used to control viscosity of the media, increase the strength of the gel and provide another means for modifying the gel to provide different levels of sample migration inhibition. Suitable cross-linking agents include disuccinimidyl suberate (DSS), 3,3'-dithiobis(sulfosuccinimidylpropionate) (DTSSP), bis(sulfosuccinimidyl)-suberate(BS3), dithiobis (succinimidylpropionate) (DSP), the combination of 3-(2,5-dioxo-1H-pyrrolyl)-propanoic acid (DPA), 3-(2-furyl)propanoic acid (FPA) modified PAEI's and DPA-modified PAEI treated with dithiols (e.g. dithiothreitol) and dithioerythritol and DPA-modified PAEI cross-linked with the free amine groups from partially hydrolyzed PAEI.

Figure 2:
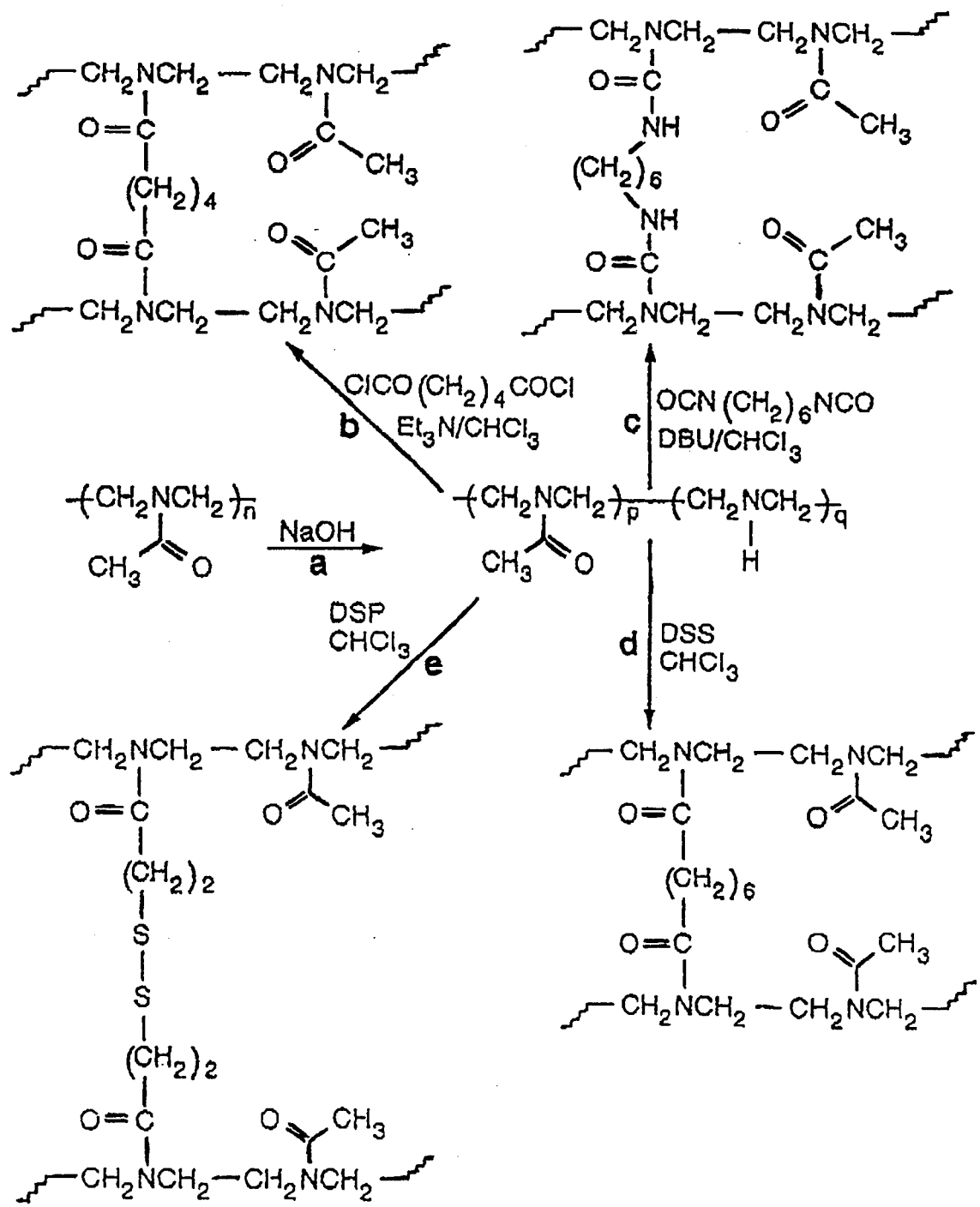
FIG. 2 is a schematic representation of four exemplary pathways for cross-linking poly(N- acetylethylenimine).

Exemplary preferred procedures for cross-linking poly(N-acylethylenimide) polymer gels in accordance with the present invention are shown in FIG. 2. In step a, the linear polymer is partially hydrolyzed with NaOH or other suitable strong base. This causes a fraction of the acyl groups attached to the polymer backbone nitrogens to be displaced leaving secondary amine groups in the polymer. These amine sites are used to crosslink the polymer. The cross-linking step (step b, c, d or e) is accomplished by mixing the linear polymer with an appropriate cross-linker in organic solution. The solution is then poured onto a plate or into an appropriate mold and the solvent is allowed to evaporate. The resulting solid state mixture may be heated to complete the reaction.

Figure 3:
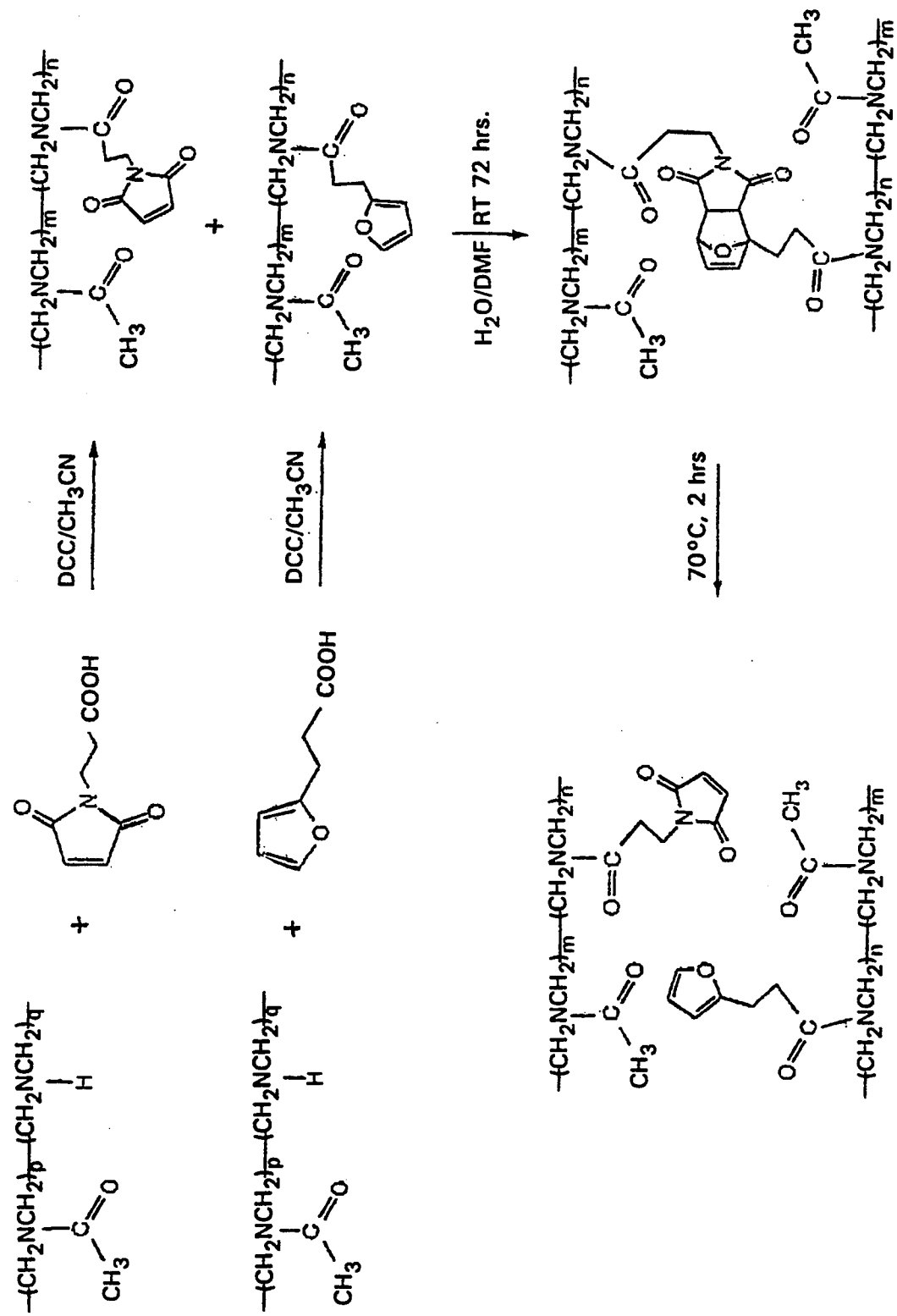
FIG. 3 is a schematic representation of an alternate exemplary pathway for forming cross-linked poly(N-acetylethylenimine).

An alternate preferred procedure for cross-linking the polymer gel is shown in FIG. 3. In this procedure, two batches of partially hydrolyzed PAEI are separately DCC-coupled through their amine sites to the carboxyl groups of 3-(2,5-dioxo-1H-pyrrolyl)propanoic acid (DPA) and 3-(2-furyl)propionic acid (FPA). The resulting DPA-modified polymer and FPA-modified polymer are dissolved in gel electrophoresis buffer and mixed together. The resulting pre-gel is then poured into an electrophoresis mold (slab or tube). Crosslinking occurs in the mold by the Diels-Alder reaction between the maleimide groups on the DPA-modified PAEI and the furyl groups on the FPA-modified PAEI.

The amount of cross-linking agent used in any particular electrophoresis support media can be varied widely depending upon the desired level of sample migration inhibition. The amount of cross-linking agent added can range from 0 mole percent to 50 mole percent of monomer. Preferably, the amount of cross-linking agent added will not exceed 10 mole percent for most applications.

Acrylamide, acrylamide derivatives, and poly acrylamide may be grafted onto PAEI's and used as separation matrices. Also the different monomers can be copolymerized.

The porosity of the support media in accordance with the present invention may be varied widely depending upon the particular monomer, degree of polymerization, particular cross-linking agent, if any, and the degree of cross-linking. The differential migration velocity of a given protein is recognized as an indication of media porosity. To achieve desired pore sizes, the above listed parameters may be varied until the desired differential migration velocity of a particular protein is obtained.

The polymer gels of the present invention are used in the same manner as acrylamide gel slabs or columns. The preparation of electrophoresis support media is described in detail in a number of references including: 1) ELECTROPHORESIS—Theory, Methods, and Applications,Vol. 2, edited by Milan Bier (Academic Press, 1967); 2) GEL ELECTROPHORESIS OF PROTEINS, edited by Michael J. Dunn (Wright Bristol, 1986); 3) The Practice of Quantitative Gel Electrophoresis by Andreas Chrambach (Advanced Methods in the Biological Sciences, IRL Press Limited, 1982); 4) GEL ELECTROPHORESIS OF NUCLEIC ACIDS—A Practical Approach, edited by D. Rickwood an B. D. Hames (IRL Press, 1990).

The polymer electrophoresis support media made with the above monomers in accordance with the present invention are particularly well-suited for use in two dimensional electrophoresis systems. Such systems are described in detail in "METHODS: A Companion to Methods in Enzymology, Volume 3, No. 2, October, pp. 98–1081991. The contents of this reference, as well as all of the other cited articles and references disclosed herein, are hereby incorporated by reference.

The electrophoresis support media in accordance with the present invention is well-suited for use with both aqueous and organic electrophoresis solvents. The use of organic solvents in electrophoresis is important for separating hydrophobic materials. Typical organic solvents which can be used in combination with the electrophoresis media include alcohols, dimethyl formamide (DMF), dimethyl sulfoxide (DMSO), tetramethylurea (TMU), formamide, tetramethylene sulfone, chloral hydrate, N-methyl acetamide, N--methyl pyrollidone and phenol. As is well known, a variety of aqueous and organic solvents may be added into the monomer mixture during formation of the electrophoresis gel. For example, the polymerization of polyacrylamide takes place in the presence of a substantially aqueous solvent. When amounts of water miscible solvents such as DMF, DMSO or TMU are added to the acrylamide polymerization mixture, the mechanical strength and clearness of the polymerized gel are severely compromised. The monomers in accordance with the present invention, however, may be polymerized in the presence of organic solvents without adversely affecting the mechanical strength, clearness or other properties required for a suitable electrophoresis support media. Mixed solvents which include high levels of water-miscible organic solvents (i.e. greater than 30 weight percent) may be used.

Gels in accordance with the present invention can be formed in 100% of many organic solvents like DMSO, DMF, formamide, methanol and ethanol. Such gels are of use in separation of small organic molecules.

Examples of practice are as follows:

MATERIALS

2-Methyl-2-oxazoline, methyl trifluoromethane sulfonate (methyl triflate), hexamethylene diisocyanate, ethyl isocyanate, adipoyl chloride, and all solvents used in literature-based syntheses were dried with agents described in the literature (cited below) and then distilled under vacuum. These substances and the precursors used in the syntheses of 3-(2,5-dioxo-1H-pyrrolyl) propanoic acid (DPA) and 3-(2-furyl) propanoic acid (FPA) were all obtained as the highest grade purity available from Aldrich. The exception to this was the palladium (2%) on strontium carbonate which was received from Pfaltz and Bauer for the synthesis of FPA. All substances were pre-treated as described in the published syntheses (cited below) except when otherwise noted. Disuccinimidyl suberate (DSS), 3,3'-dithiobis (sulfosuccinimidylpropionate) (DTSSP), bis (sulfosuccinimidyl) suberate (BS3), and dithiobis (succinimidyl-propionate) (DSP) were purchased from Pierce. All electrophoresis reagents and standards were obtained as electrophoresis grade from Bio-Rad.

SYNTHESIS OF PAEI

As a typical procedure, 50 g (588.2 mM) of freshly distilled 2-methyl-2-oxazoline was added to a 250 ml Schlenck tube (Kontes, Vineland, N.J.) equipped with a stir bar. Dried argon was passed through the stirred monomer solution for 10 minutes while it was being heated in an oil bath at 90° C. Under argon, 0.48 g methyl triflate (2.9 mM) was added by syringe and the top valve of the Schlenck flask was closed quickly. An exotherm was observed 30 seconds after the addition of the methyl triflate. The polymerization was allowed to proceed for 36 hrs. at 90° C. It is important to note that the entire level of the reaction mixture (not the entire flask) must be submersed in the oil bath during polymerization. The unreacted monomer was decanted while the crude PAEI was dissolved in warm methanol and precipitated twice with ether. The polymer was once again dissolved in anhydrous MeOH and rotovapped to a dry yellow powder. Yield was 42.2 g (84%). Significantly lower yields were obtained in larger flasks.

PARTIAL HYDROLYSIS OF PAEI

The procedure described in Chujo, Y., Yoshifuji, Y., Sada, K., and Saegusa, T. (1989) Macromolecules 22, 1074, was followed with the following modifications. After heating in sodium hydroxide solution, the pH of the polymer solution was neutralized by dropwise addition of HCl while stirring. The polymer was then dialyzed two times in water and then twice more in MeOH (no more than three hours for each MeOH dialysis) with 1000MW Cut-off Spectrapore Dialysis Tubing (Spectrum). The degree of hydrolysis was monitored by 1H NMR by determining the integral ratio between the signals from the methylene protons adjacent to a secondary amino group and the methylene protons adjacent to an acetamide group.

SYNTHESIS OF FPA AND DPA AND COUPLING OF THEM TO HYDROLYZED PAEI

The synthesis of these crosslinkers essentially followed the procedures described in Chujo, Y., Sada, K., and Saegusa, T. (1990) Macromolecules 23, 2636; Railings, R. J. and Smith, J. C. (1953) J. Chem. Soc., 18; and Rajagopolan, S. and Raman, P. V. A. (1945) Org. Synth. 25, 51. These and the precursor reactions were scaled-up at least two-fold without significantly lowering the reported yields. The identity of the intermediates and products were confirmed by NMR, IR, and melting points. Some variations on the published procedure for the dicyclohexylcarbodiimide (DCC)-mediated coupling of DPA and FPA to partially hydrolyzed PAEI were performed. For example, at times the dicyclohexylurea (DCU) produced as a by-product of these reactions could not be entirely separated from the polymer product through filtration and precipitation with ether. In these cases, the polymer product was dissolved in a minimum of MeOH and then water was slowly added until the DCU started to come out of solution. At this point, a small amount of MeOH was added to resolubilize the DCU. The solution was cooled at 4° C. overnight to crystallize the DCU, which was later removed by filtration.

REACTIONS OF PARTIALLY HYDROLYZED PAEI WITH HEXAMETHYLENE DIISOCYANATE AND ADIPOYL CHLORIDE

Typically, one gram of partially hydrolyzed polymer was dissolved in 2 mls of chloroform. More chloroform is sometimes needed if the amount of hydrolysis is high, 5%. To this solution, the hexamethylene diisocyanate or adipoyl chloride was added quickly while the polymer solution was being vigorously stirred. A 1:1 molar ratio of isocyanate or acyl chloride groups from adipoyl chloride to secondary amine groups on the partially hydrolyzed polymer was used. When adipoyl chloride was used, a 1:1 molar ratio amount of triethylamine accompanied its addition. After addition of the crosslinker, the reaction mixture was quickly poured onto a square (7×7 cm) glass area bounded by polytetrafluoroethylene spacers. The chloroform was allowed to evaporate in a fume hood, after which the reaction was placed in an oven for 6 hrs. at 50° C. The resulting film was soaked in MeOH 2×4 hrs. and then water 2×8 hrs. The swelled gel was then allowed to equilibrate in the appropriate solution for electrophoresis experiments. Yield of redried film was 96%.

ETHYL ISOCYANATE CAPPING

An amount of ethyl isocyanate equal to the molar amount of original amine sites contained in the partially hydrolyzed PAEI was mixed with 1/100 of the molar amount of 1,8-Diazabicyclo [5.4.0.]undec-7-ene (DBU) in 20 ml chloroform. This solution was poured into a polyethylene container, and the film (before MeOH and water soaks) from the above procedure was immersed in the solution. The lid was placed on the container and the reaction was allowed to proceed for 8 hrs. at 50° C.

CROSSLINKING OF PAEI WITH DSP AND DSS (1.8 g, 4.5 mM) of DSP or (1.7 g, 4.5 mM) of DSS was dissolved in 2 ml chloroform. The crosslinker was added to a 2 ml solution of 1.0 g of 5.0% hydrolyzed PAEI (6.0 mM amine sites). The solution was stirred for 10 minutes and then poured to form a 7×7 cm film. The chloroform was allowed to evaporate and the reaction was placed in an oven at 50° C. for 36 hrs. Excess reactant and impurities were removed by soaking in chloroform. Yields for the DSP and DSS reactions were 76 and 80%, respectively. The disulfide links in this DSP-modified PAEI gel were reduced with a five-fold molar excess (2.3 g, 30 nM) of 2-mercaptoethanol in 20 ml water. The gel became a relatively non-viscous solution after 36 hrs. of reaction at 22° C.

ISOELECTRIC FOCUSING (IEF) ELECTROPHORESIS

Diisocyanate Gels

The purified hexamethylene diisocyanate-crosslinked film was equilibrated for 24 hrs. in a 12 ml aqueous solution containing 0.5 ml 3–10 BioRad Ampholyte Solution and 0.25 ml 5–7 Biorad Ampholyte Solution. A 3 cm×5 cm×0.075 cm piece of this gel was cut out and placed on a Pharmacia FBE-3000 Flat Bed Electrophoresis Apparatus. 5 ul solutions of proteins (pre-stained Biorad IEF Standards, high and low molecular weights) were spotted 1 cm from the lengthwise edge of the gel. Cotton strips soaked in 6 mM $H_3PO_4$ at the anode and 10 mM NaOH at the cathode were placed on top of the gel. The electrodes were in turn placed on top of the strips. The electrophoresis was performed at a constant 200V unless otherwise stated.

FPA-DPA Gels

In all studies, a mixture of FPA-modified PAEI and DPA-modified PAEI was made so that the total number of FPA and DPA units were equal. Slab gels were 9.0 cm×7.5 cm×0.075 cm and usually contained five wells. 0.550 g of 5.0% FPA-modified PAEI (0.0062M reactive unit) and 0.559 g of 5.0% DPA-modified (0.0062M reactive units) were dissolved in 2 ml of dimethylformamide. It is advisable to minimize exposure of the DPA and FPA-modified polymers to light once they are in solution as fluorescent by-products (maximum emission at 430 nm) may be formed. For non-denaturing gels, this polymer mixture was then added to 9 mls of aqueous solution containing the 0.4 ml 3–10 BioRad Ampholyte Solution and 0.2 ml 5–7 BioRad Ampholyte Solution. For denaturing gels, the 9 ml solution contained the same amount of ampholytes in addition to 8M urea and 0.27 g CHAPS. The solution was allowed to solidify (i.e. the crosslinks "cured") for 72 hrs. in the dark before electrophoresis.

The electrophoretic apparatus is described in Zewert, T. E. and Harrington, M. J. (1992) Electrophoresis 13, 824–831. The upper and lower buffer chambers contained 10 mMNaOH and 6 mM $H_3PO_4$, respectively 2–5 uL of the BioRad IEF protein standards were loaded per well and electrophoresis was performed at constant voltage, 200–800V per gel. Protein migration and IEF was directly observed, extending over periods of 2–12 hours.

Tube gels were made (usually twelve at a time) from a stock solution of 5 ml which contained the same proportion of components used in the slab gel studies. 0.4 ml of the solution was added to each test tube. A glass tube (1.4 mm inside diameter and 200 mm long) was placed in each of the test tubes, and the solution was carefully sucked into the tubes by a syringe which was attached to each electrophoresis tube by polyvinylchloride tubing. The solution was kept in the electrophoresis tube by the vacuum created by the syringe (an airtight seal is thus essential) until solidification occurred. This time was typically 24–36 hrs for a 10%T gel, but the solution was allowed to cure for 72 hrs. total before the gel run. A BioRad Model 175 Tube Gel Apparatus was used for electrophoresis, which was performed with the same electrolytes as described above, for time periods varying from 2–18 hrs, at constant voltage that was varied in different experiments from 200–2000V. IEF was considered complete when the protein migration was minimal and the current had reached a stable 0.1–0.2 mA.

The hexamethylene diisocyanate-crosslinked gels focused colored protein standards in a similar time and with high resolution comparable to parallel runs of polyacrylamide gels. The FPA/DPA gels also gave clear resolution of IEF standards. Under the non-denaturing conditions, more bands of IEF standards were seen in PAEI gels than in parallel polyacrylamide gels. Less cathodic drift was observed in equivalent %T PAEI gels than in polyacrylamide gels. With denaturant in the PAEI gels, the resolution and focusing times were similar and the cathodic drift was still less than with polyacrylamide. With higher %T in the PAEI gels, greater resolution was achieved at the expense of much slower focusing.

The above examples show that poly(N-acylalkylenimine) (crosslinked PAEI) can be used for IEF electrophoresis. Of the several crosslinker systems described above, the DPA/FPA modified PAEI is the most convenient for laboratory use because the crosslinked gel is easily molded while in a solvent appropriate for electrophoresis. Also, the DSP and DPA/FPA systems can be used for reversible gelation. PAEI crosslinking with hexamethylene diisocyanate, adipoyl chloride, and DSP can only be performed in non-aqueous conditions to produce films. However, these conditions are amenable to industrial processes. Rolls of crosslinked PAEI film can be manufactured that could be later hydrated for electrophoresis. The dried, crosslinked PAEI films are mechanically flexible enough for such manipulations. The result could be a reproducible, convenient matrix for electrophoresis. Bisoxazolines could also be used as crosslinkers. However, these crosslinkers would be practical only if the film could be formed during polymerization.

An advantage of PAEI electrophoresis gels is that they are much more resistant to hydrolysis by base than polyacrylamide. PAEI can be placed in 1M NaOH (pH 14) for days without any detectable hydrolysis of the N-acetyl group. On the other hand, polyacrylamide shows significant hydrolysis at pH 10–11 in a few hours. Hydrolysis of polyacrylamide causes a deterioration of mechanical strength and an increase in electroendosmosis of the gel. These problems often occur when the gel is exposed to high pH in DNA and IEF separations, and in prolonged storage of protein SDS gels. It is expected that the greater stability of PAEI gels with regard to hydrolysis will lead to more stable gels during such DNA and IEF separations.

The references referred to above are hereby incorporated by reference. Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. An electrophoresis support media comprising a polymer gel which is in a shape suitable for use in electrophoresis, wherein said polymer gel includes at least one sample receiving location where a sample to be analyzed is applied to said polymer gel, said polymer gel comprising a polymer having the formula

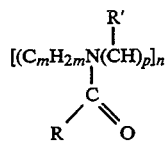

wherein m and p are between 1 and 3, n is between about and 10,000, where R is an alkyl, perfluoroalkyl or phenyl group and wherein R' is H or an alkyl group.

2. An electrophoresis support media according to claim 1 wherein R is an alkyl group having from 1 to 20 carbon atoms.

3. An electrophoresis support media according to claim 2 wherein R is a methyl group.

4. An electrophoresis support media according to claim 1 wherein R is a perfluoroalkyl group selected from the group consisting of $-CF_3$, $-C_2F_5$, and $-C_3F_7$, $-C_7F_{15}$.

5. An electrophoresis support media according to claim 1 wherein R is a phenyl group selected from the group consisting of $-C_6H_5$, $-p-NO_2C_6H_4$, and $-p-CH_3C_6H_4$.

6. An electrophoresis support media according to claim 1 wherein said polymer is cross-linked.

7. An electrophoresis support media according to claim 3 wherein R' is hydrogen.

8. An electrophoresis support media according to claim 1 wherein said polymer gel comprises an electrophoresis support medium.

9. An electrophoresis support media according to claim 1 wherein said polymer gel is in the shape of a slab.

10. An electrophoresis support media according to claim 1 wherein said polymer gel is in the shape of a column.

11. An electrophoresis support media according to claim 1 wherein m and p are 1.

12. In an electrophoresis method wherein a sample is subjected to electrophoretic migration through an electrophoresis support media, the improvement comprising providing an electrophoresis support media comprising a polymer gel comprising a polymer having the formula

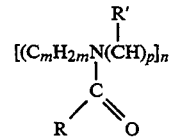

where m and p are between 1 and 3, n is between about 100 and 10,000, where R is an alkyl, perfluoroalkyl or phenyl group and wherein R' is H or an alkyl group.

13. An improved electrophoresis method according to claim 12 wherein R is an alkyl group having from 1 to 20 carbon atoms.

14. An improved electrophoresis method according to claim 13 wherein R is a methyl group.

15. An improved electrophoresis method according to claim 12 wherein R is a perfluoroalkyl group selected from the group consisting of $-CF_3$, $-C_2F_5$, and $-C_3F_7$, $-C_7F_{15}$.

16. An improved electrophoresis method according to claim 12 wherein R is a phenyl group selected from the group consisting of $-C_6H_5$, $-p-NO_2C_6H_4$, and $-p-CH_3C_6H_4$.

17. An improved electrophoresis method according to claim 12 wherein said polymer is cross-linked.

18. An improved electrophoresis method according to claim 14 wherein R' is hydrogen.

19. An improved electrophoresis method according to claim 12 wherein m and p are 1.

* * * * *